United States Patent [19]

Augustine et al.

[11] Patent Number: 4,819,619
[45] Date of Patent: Apr. 11, 1989

[54] DEVICE FOR INSERTING A NASAL TUBE

[76] Inventors: Scott D. Augustine, 1601 Stonecrest Ct.; Douglas J. Augustine, 503 S. 23rd St., Both of Blue Springs, Mo. 64015

[21] Appl. No.: 3,752
[22] Filed: Jan. 16, 1987
[51] Int. Cl.[4] ............................................. A61M 16/00
[52] U.S. Cl. ........................ 128/200.26; 128/207.14; 128/207.18; 128/341; 604/170; 604/280
[58] Field of Search .................... 128/200.26, 207.18, 128/207.14, 207.15, 341, 342, 343, 772; 604/170, 280, 281, 282, 265

[56] References Cited

U.S. PATENT DOCUMENTS

| | | | |
|---|---|---|---|
| 1,879,307 | 9/1932 | Kennedy | 128/341 |
| 1,957,673 | 5/1934 | Sayre | 128/341 |
| 2,458,305 | 1/1949 | Sanders | 604/282 |
| 2,862,498 | 12/1958 | Weekes | 128/207.14 |
| 3,077,194 | 2/1963 | Walden et al. | 128/343 |
| 3,260,258 | 7/1966 | Berman | 128/342 |
| 3,511,243 | 5/1970 | Toy | 128/200.26 |
| 3,754,554 | 8/1973 | Felbarg | 128/351 |
| 3,802,440 | 4/1974 | Salem et al. | 128/351 |
| 4,175,564 | 11/1979 | Kwak | 128/350 R |
| 4,182,342 | 1/1980 | Smith | 604/265 |
| 4,186,745 | 2/1980 | Lewis et al. | 604/265 |
| 4,211,234 | 7/1980 | Fisher | 128/200.26 |
| 4,244,362 | 1/1981 | Anderson | 128/200.26 |
| 4,256,099 | 3/1981 | Drysen | 128/200.26 |
| 4,327,721 | 5/1982 | Goldin et al. | 128/207.15 |
| 4,327,735 | 5/1982 | Hampson | 128/348 |
| 4,332,242 | 6/1982 | Chikama | 128/200.26 |
| 4,402,684 | 9/1983 | Jessup | 604/282 |
| 4,405,308 | 9/1983 | Jessup | 128/207.14 |
| 4,636,200 | 1/1987 | Vaillancourt | 604/170 |
| 4,655,214 | 4/1987 | Linder | 128/207.14 |

FOREIGN PATENT DOCUMENTS 257979 3/1913 Fed. Rep. of Germany ...... 128/342
2928635 2/1981 Fed. Rep. of Germany ........................ 128/207.14

OTHER PUBLICATIONS

Grants Atlas of Anatomy, J.C.B. Grant, 6th Edition, 1972, Williams & Wilkins Co., Baltimore, MD.
Extract from the *Annals of Emergency Medicine*, p. 36/143, 10:3 (Mar.), 1981.

Primary Examiner—Edward M. Coven
Assistant Examiner—J. P. Lacyk
Attorney, Agent, or Firm—Baker, Maxham, Jester & Meador

[57] ABSTRACT

A device for inserting a nasal tube through the nose into the oropharynx includes an elongate, collapsible sleeve to which is attached an elongate, relatively slender arcuate member extending along a longitudinal dimension of the sleeve for guiding it through the nasal cavity and nasopharynx. The sleeve has openings at its distal and proximal ends. A soft, blunt distal tip is formed at the distal end of the device extending beyond the distal end opening in the sleeve for extending into the oropharynx. Once the device is in place, a tube can be inserted through the sleeve and guided through the nose to the oropharynx. A dilating member formed from a resilient, compressible material may be used to erect the sleeve and dilate the nasal passageway, if necessary.

20 Claims, 2 Drawing Sheets

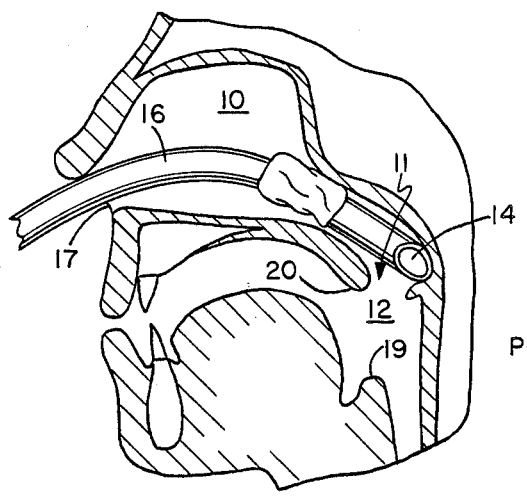
FIG. 1
PRIOR ART
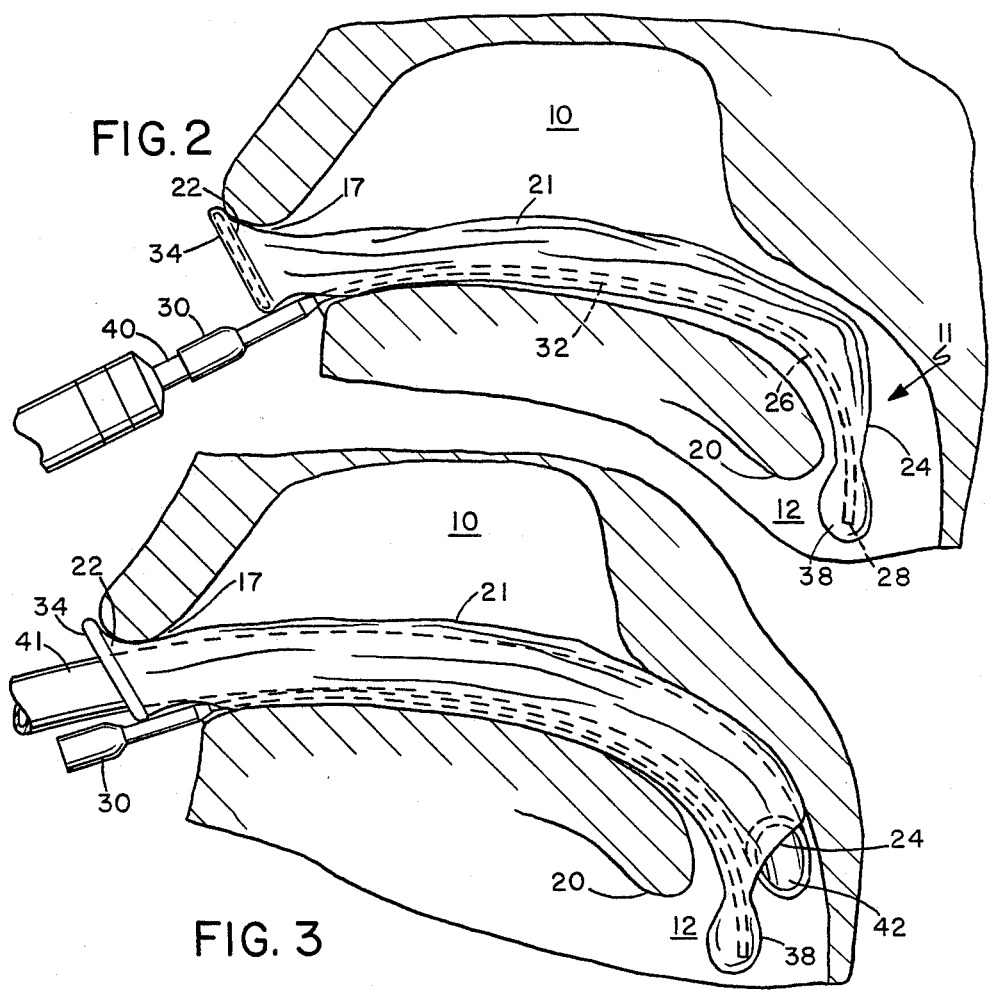
FIG. 2
FIG. 3

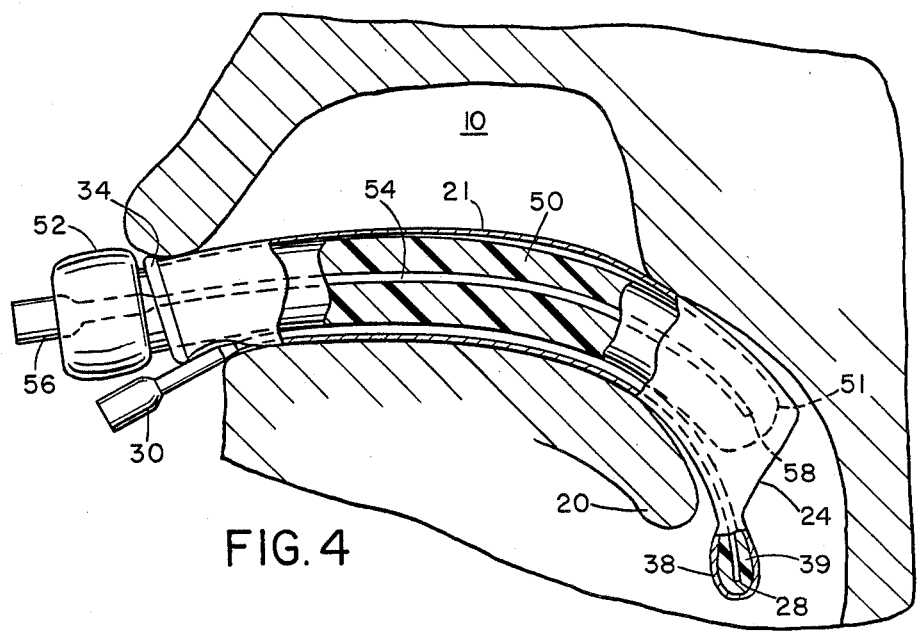
FIG. 4
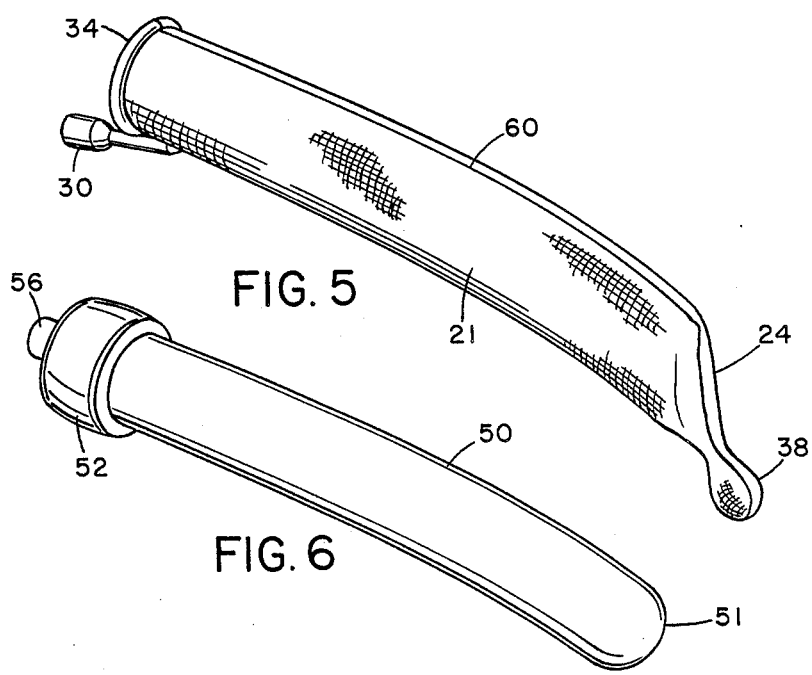
FIG. 5
FIG. 6

DEVICE FOR INSERTING A NASAL TUBE

BACKGROUND OF THE INVENTION

The invention is in the field of inserting a nasal tube through the nose into the trachea or esophagus of a patient.

As is known, endotracheal and naso-gastric tubes are inserted into a patient through the nose for purposes which include the administration of anesthesia, ventilation of airways, and pumping of stomach fluids.

When intubation is through the nose, the attending physician can encounter a number of potential problems. Customarily, the intubation consists of simply inserting a flexible plastic hollow tube through a nostril, feeding it through the nasal cavity, the nasopharynx and oropharynx into the trachea or esophagus.

As is known, nasal intubation can traumatize the nasal mucosa, causing bleeding. Such trauma can result from laceration of - or formation of a submucosal "false channel" through - the mucosa. Often it is difficult to distinguish the resistance of mucosa from the resistance presented by the turbinates and a tube can be channeled through the mucosa with the application of sufficient pressure.

Insertion of an endotracheal tube through the nasal passageway is greatly facilitated by application or a local anesthetic to the mucosa in order to relieve discomfort. Frequently, in order to decrease mucosal swelling and to suppress bleeding resulting from abrasion of the mucosa, a vasoconstrictor is also applied topically. Presently, there is no effective way to topically apply an anesthetic or a vasoconstrictor in the nasal passageway prior to or concurrently with intubation.

Nasal insertion of an endotracheal tube frequently results in the transport of bacteria-laden mucus from the nose and nasopharynx to the trachea. This can result in pneumonia or systemic infection, as is borne out by the frequent incidence of measurable blood-borne bacteria after nasal intubation.

Finally, difficulty is often encountered in "making the corner" between the nasal cavity an the oropharynx; as shown in FIG. 1, the near 90° transition between the nasal cavity 10 and the oropharynx 12 is difficult to traverse and the tip 14 of an endotracheal tube 16 can lacerate or perforate the posterior wall of the oropharynx in attempting to round the corner.

A number of prior art devices are available for facilitating the introduction of tubes into the trachea or esophagus. Such devices are primarily for guiding tubes through the oropharynx into the proper passageway. In this regard, a naso-gastric tube insertion guide is disclosed in U.S. Pat. No. 4,175,564, which teaches the use of an arcuate, perforated tube formed from rubber or plastic which is fed through the mouth into the pharynx and then the esophagus. A naso-gastric tube is then fed through the positioned guide to the stomach. If used in the nose, this guide would pose the same danger to the nasal mucosa and posterior pharynx as the naso-gastric tube itself: the sharp edges of the distal end of the guide can abrade or channel through the nasal mucosa and lacerate the rear of the oropharynx during insertion. Further, such a guide makes no provision for topicalization with local anesthetics prior to or during insertion. Another curved guide tube for feeding an endotracheal tube through the mouth into the trachea is taught in U.S. Pat. No. 4,211,234. Again, this guide can traumatize throat tissue and has no provision for topicalization.

The prior art also provides other means for feeding tubes through curved bodily passageways by the provision of guide tubes having contours which conform to the contour of the passageways (U.S. Pat. No. 3,754,554) or by flexible members which are manipulated by an operator to assume the contour of a passageway into which at tube is being fed (U.S. Pat. Nos. 3,802,440 and 4,244,362).

None of the prior art intubation guide devices address the problems discussed above. Their use in the nose would still present the potential of tissue injury and the devices make no provision for topicalization.

SUMMARY OF THE INVENTION

The invention is founded upon the critical observation made by the inventors that tissue traumatization during tubal insertion can be avoided by providing a protective channel through the nose which is contoured to guide a nasally-inserted tube into the oropharynx. In the invention, this channel has the form of a protective sleeve. It was also observed that construction of the protective sleeve from a fluid-wicking material would provide a convenient means of conducting a local anesthetic to the nasal mucosa and throat passageways through which a tube is to be guided.

The inventors have further realized that effectiveness of a protective sleeve in a nasal cavity occluded by swollen nasal tissue can be enhanced by provision of a dilator to dilate the passageway through the swollen tissues prior to insertion of a tube.

The invention is expressed from one aspect as a device for introducing a nasal tube which includes an elongate, porous sleeve formed from a collapsible material, the sleeve forming a generally tubular passageway having proximal and distal openings. The device also includes an elongate, relatively slender, arcuate guiding member attached to the sleeve along a longitudinal sleeve dimension extending between the proximal and distal openings. A soft, blunt distal tip is formed on the the guiding member and extends beyond the distal opening. The device is inserted, distal tip first, through a nostril and is fed through the nasal cavity and nasopharynx to the oropharynx where the arcuate shape of the guiding member conforms the sleeve to the 90° corner in the nasopharynx connecting the nasal cavity with the oropharynx. Thus positioned, the sleeve provides a protective passageway for the insertion of a tube, and also provides a fluid-conducting means for topicalizing the nasal tissue with local anesthetics.

In consideration of the inventor's observation concerning swollen nasal tissue, the invention extends also to a dilating device for dilating a nasal passageway, which consists of an elongate, arcuate dilating member formed from a resilient, porous material which is compressed when inserted into a nasal passageway. The dilating device includes a member having a blunt, rounded distal end and a proximal end. The device also includes a stop formed on the proximal end for preventing the entry of the proximal end into a nasal opening when the member is inserted into a nostril, distal end first. The dilating device is completed by provision of an arcuate, relatively slender, pliable stylet disposed substantially in the central axis of the dilating member. When inserted through a nostril, distal end first, the device displaces swollen tissue and opens a passageway for intubation. Since the dilating member is formed from a porous material, the dilated passageway can be topicalized by fluid local anesthetics conducted through the member.

The invention also resides in an apparatus which combines the nasal tube introducing device and the dilating device into an apparatus for introducing a tube into a dilated nostril. The apparatus includes a tube introducer having an elongate, porous sleeve formed form a collapsible material and including proximal and distal openings. The introducer also includes an elongate, relatively slender, arcuate guiding member attached to the sleeve along a longitudinal sleeve dimension extending between the proximal and distal openings. The introducer has a soft, blunt distal tip formed on the the guiding member and extending beyond the distal opening of the sleeve. The apparatus combines the tube introducer with a nasal passageway dilator having a dilating means formed from a resilient, porous material and insertable into the sleeve for erecting the sleeve from a collapsed, compact configuration into a tubular configuration and for dilating the nasal passageway into which the tube introducer has been inserted. The dilating means is compressible when inserted, through the sleeve, into a nasal passageway. The dilator also includes means for conducting fluid from outside a nostril opening to the dilating means when the dilating means is inserted into a nostril through the sleeve.

Finally, the invention is embodied in a method of introducing a tube through a body orifice. In a first step, an elongate, porous sleeve is placed into an elongate collapsed configuration. The sleeve in the collapsed configuration is inserted into a bodily orifice with one end extending out of the orifice. After introduction of the sleeve into the bodily passageway communicating with the orifice, a tube is introduced into the orifice by inserting the tube into the sleeve through the end of the sleeve which extends out of the orifice.

A principal object of the summarized invention is to prevent injury to nasal tissues during nasal intubation.

Another object of the invention is to provide for effective topicalization of nasal tissue with local anesthetics, prior to or during intubation.

Still another object is to prevent the transport of bacteria-laden mucus from the nasal passageway into the trachea.

Finally, an object of the invention is to effectively guide a tube around the corner from the nasal cavity into the oropharynx, while preventing pharyngeal laceration resulting from intubation.

These objects and other attendant advantages of the invention will be manifest with a reading of the following description in connection with the below-summarized drawing figures.

BRIEF DESCRIPTION OF THE DRAWINGS

FIG. 1 illustrates conventional nasal intubation.

FIG. 2 illustrates the positioning of a device according to the invention for introducing a nasal tube, with the device shown in cross-section, in the collapsed configuration.

FIG. 3 illustrates the device of FIG. 2 in position, facilitating nasal intubation.

FIG. 4 illustrates the device of FIG. 2 in combination with a dilating device.

FIG. 5 is a perspective view of the device of FIG. 2 in an erected configuration.

FIG. 6 is a perspective view of the dilating device.

DETAILED DESCRIPTION OF THE PREFERRED EMBODIMENT

Referring again to FIG. 1, the application environment of the invention can be understood. The nasopharyngeal space 10, 11, 12 is shown in the cutaway side view of FIG. 1. The space is entered through a nostril 17. Initial penetration into the space passes through the nasal cavity 10, makes the curve in the nasopharynx 11, past the uvula 20, into the oropharynx 12 and drops down through the oropharynx to the epiglottis 19. All nasal intubation follows the path whether the destination is the trachea or the esophagus. Prior art intubation is characteristically performed as illustrated in FIG. 1 and consists of feeding a tube such as the endotracheal tube 16 through the nostril along the path just described.

The invention can be understood with references to FIGS. 2–4. FIG. 2 illustrates the upper portion of the cutaway view of the nasopharyngeal space illustrated in FIG. 1, and shows a device for introducing a tube into the space.

In FIG. 2, the device for introducing a nasal tube includes an elongate, porous sleeve 21 which is formed from a collapsible material, suitable for wicking or conducting fluid. The sleeve 21 forms an elongate protective sheath having a proximal opening 22 and a distal opening 24. An elongate, relatively slender arcuate guiding member 26 is attached to the sleeve 21 along a longitudinal dimension extending generally between the proximal and distal openings 22 and 24. The guiding member can comprise a stylet or relatively slender catheter. The guiding member 26 includes apertured distal and proximal tip 28 and 30 connected by an interior channel 32. A stop 34 is formed on the proximal opening 22 of the sleeve 21 and comprises, for example, an annular ring or collar made of a non-collapsible material which possesses a flexibility that is somewhat less than the flexibility of the sheath material.

A blunt, rounded distal tip 38 is formed on the end of the device and covers and surrounds the distal tip 28 of the guiding member 26. As seen in FIG. 4, the tip 38 is formed by a padding of spongy, porous material 39 which is enclosed by a lower extension of the sleeve 21, the lower extension protruding outwardly from the portion of the sleeve below the distal opening 24. FIG. 2 also shows the pronounced curvature of the tube introduction device, which results from the arc formed in the guiding member 26.

In use, the device is inserted, distal tip 38 first through the nostril 17, and is fed through the nasal cavity 10 and nasopharynx 11 into the oropharynx 12. A can be appreciated, the soft, blunt distal tip 38 significantly reduces the prospect of abrading, lacerating, or penetrating the nasal mucosa or the posterior wall of the nasopharnx 11. The guiding member 26 imparts a relative stiffness to the device which permits it to be advanced through the nasopharyngeal space 10, 11, 12 by pressure applied to the proximal portion of the guiding member 26. The curvature of the device essentially conforms it to the curvature of the space being traversed and enables the device to "make the curve" in the nasopharynx 11. For this purpose, the guiding member may, for example, have curvature approaching ninety degrees. The stop 34 formed on the proximal opening 22 of the sleeve 21 prevents the device from being inserted altogether into the nostril and retains the proximal opening 22 in place just outside the nostril 17. While the device is being inserted through the nostril, it will be appreciated that the collapsible property of the sleeve 21 will permit the sleeve to conform to the interior terrain of the nasal cavity 10. Thus, if the nasal mucosa are swollen, the sleeve 21 will be relatively fully collapsed, yet will form a dilatable, protective channel within the nasal passageway.

Topicalization of the nasal cavity with local anesthetics is accomplished by the guiding member 26. As the device is being inserted into the nasal passageway, a local anesthesia and/or a vasoconstrictor can be fed in fluid form from a syringe 40 which is in communcation with the apertured distal tip 30 of the member 26. The fluid is conducted through the channel 32 to the apertured distal tip 28, where it exits into the material 39 of the blunt distal tip 38. Since the material 39 and the material of the sleeve 21 are porous, the fluid exiting the distal tip 28 will be conducted to the outer surface of the sleeve 21 whence it will be transferred by contact to the pharyngeal tissue. It should be evident that pin holes can be also made along the length of the member 26 to facilitate a more evenly-distributed condition of fluid from the channel of the member to the sleeve 21. Thus, effective topicalization of the nasal passageway can be accomplished by the device as the device is being inserted into the passageway, and can be continued for so long as the device is in place in the passageway.

Prior to insertion, the distal opening 24 is sealed preferably by a relatively weak adhesive or heat seal which yields with little resistance to a probing force exerting through the sleeve 21 in the direction of the distal opening 24. This sealing will prevent the migration of mucus and other bacteria-laden material into the sleeve 21 while it is being inserted. This preserves the prophylactic nature of the passageway and effectively reduces the chance of infection because the tube is being fed through the sleeve 21.

With reference now to FIG. 3, the use of the tubeintroducing device of the invention can be understood. When the device is fed through the nasal passageway, it forms a protective tubular channel through which a tube 41 can be fed. The channel protects the pharyngeal tissue from injury and penetration, keeps the tip 42 of the tube free of bacteria-bearing material, and forms a curved passageway which conforms to the transition between the nasal cavity and oropharynx. As the tube 41 is fed, tip 42 first, through the proximal opening 22 of the sleeve 21, the tube travels through the nasal passageway within the sleeve, and traverses the corner at the nasopharynx 11. At this point the tube can be fed further down the oropharynx for insertion into the trachea or the esophagus.

In FIG. 4 a nasal dilating device is illustrated in combination with the tube introducing device of FIGS. 2 and 3. The dilating device is shown in perspective in FIG. 6. The dilating device is useful for dilating a passageway between swollen nasopharyngeal tissues prior to introduction of a tube as illustrated in FIG. 3. In FIGS. 4 and 6, the dilating device consists of an elongate, arcuate dilating member 50 which is formed from a soft, porous material which is compressible, yet which resumes its original shape when compression is removed. The dilating member 50 has a blunt, rounded distal tip 51 and transitions at its proximal end to an annular nasal stop 52. Disposed and embedded in the central axis of the dilating member 50 is an arcuate, relatively slender and pliable shaft or member 54, which conforms in all essential respects to the guiding member 26 of the tube-introducing device. The central shaft is curved, and this curvature is imposed generally on the dilating member 50. The central shaft 54 has proximal and distal openings 56 and 58, respectively, that are connected by an interior channel. This permits topicalization by introduction of fluid local anesthetics into the porous material of the dilator, from a syringe attached to the proximal tip 56, which is conducted through the channel of the shaft 54 to the distal tip 58. Alternatively, the shaft can be apertured with pinholes along its length to permit a relatively even flow of fluid into the porous material of the dilating member 50. Since the dilating member material is porous, the fluid is conducted to the surface of the member, where it is transferred by contact to the nasopharyngeal tissues. As shown in FIG. 4, the dilating device can be used in combination with the tube introducing device of FIG. 2 to perform a dual function. First, the dilating device can be used after insertion of the tube introducing device to dilate a passageway between the swollen nasal tissues, for the introduction of a tube through the sleeve 21. At the same time that the swollen nasal tissue is dilated, the dilating device places the sleeve 21 into a relatively erect, open configuration through which a tube of relatively large diameter can be easily fed. The dilating device is prevented from entering wholly into the nostril by the nasal stop 52 formed on its proximal end.

It will be appreciated that the dilating device, being formed of a soft, compressible material, dose not abruptly force an opening in swollen nasal tissue. Rather, if the tissue is relatively tightly swollen, the dilating member compresses somewhat, yet gently thrusts open a passageway when inserted, distal tip first, into the sleeve 21. It will be appreciated that the blunted distal tip 51 prevents damage to nasal tissue, while the curvature of the dilating device enables it also to "make the corner."

The dilating device can be used alone, without the tube introducing device, to dilate nasal tissue. In this regard, the dilating device is simply inserted, distal tip 51 first, through a nostril and into the nasal passageway. It will be obvious that the catheter-like structure of the shaft 54 and the porosity of the material from which the dilating device is formed permit topicalization of nasal tissue while the dilator is used alone.

As illustrated in FIG. 5, the tube introducing device can be provided with a nascent slit 60 which extends, generally longitudinally, along the sleeve from the distal opening 24 to the proximal opening 22 and which transitions to the nasal stop 34. A is known, such a slit is useful for removing the device once it has been used to feed a nasal tube from the nostril into either the trachea or esophagus. When the tube is in place, the slit 60 can be perforated, beginning at the nasal stop 34 and the proximal opening 22 so that the device can be removed without disturbing the in-place tube. In this regard, as the device is withdrawn from the nose, the slit 60 is continuously perforated from the nasal stop 34 to the distal opening 24 so that the device can be removed from the tube as it is being extracted from the nasal passageway.

It will be appreciated that the detailed description and drawings are to be regarded as illustrative of the invention and that the invention may be changed, modified, or elaborated without departing from the spirit of the invention or the scope of the appended claims.

We claim:
1. A device for introducing a nasal tube, comprising:

an elongate, porous sleeve formed from a collapsible material which is non-self-sustaining and tends to collapse without internal support, the sleeve having proximal and distal ends with openings at said proximal and distal ends;

an elongate, relatively slender arcuate guiding member attached to said sleeve along a longitudinal sleeve dimension extending between said proximal and distal ends; and a soft, blunt distal tip formed on said guiding member and extending beyond said distal end.

2. The device of claim 1 further including stop means on said proximal end of said sleeve for preventing the entry of said proximal end into a nasal opening when said device is inserted into a nostril, distal tip first.

3. The device of claim 1 further including means for maintaining said distal opening closed and for yielding in response to a probing force exerted through said sleeve in a direction toward said distal end of said sleeve to open said distal end opening.

4. The device of claim 1 wherein said guiding member comprises a catheter with a distal end opening into said distal tip, a proximal end, and a fluid-conducting passageway connecting said distal and proximal ends of said catheter.

5. The device of claim 1 wherein said sleeve is formed from a material capable of conducting fluid.

6. The device of claim 1 wherein said distal tip is formed on said distal end of said sleeve and comprises a mass of woven permeable material for conducting fluid outwardly from said distal end.

7. The device of claim 1, wherein the arcuate guiding member has a curvature approaching 90 degrees for enabling the device to round the corner at the rear of the nasopharynx.

8. A device for dilating a nasal passageway, comprising:

an elongate, arcuate dilating member of generally solid construction formed from a resilient, porous material which is compressible when inserted into a nasal passageway, said dilating member having a central axis, a blunt, rounded distal end and a proximal end;

a stop means formed on said proximal end for preventing the entry of said proximal end into a nasal opening when said dilating member is inserted into a nostril, distal end first; and an arcuate, relatively slender, pliable shaft embedded substantially in the central axis of said dilating member.

9. The device of claim 8 further including channel means for conducting fluid from a location proximal to said stop means to said dilating member when said dilating member is inserted into a nostril, distal end first.

10. The device of claim 9 wherein said pliable shaft is a catheter with proximal and distal openings and is disposed in said dilating member such that said proximal opening extends out of aid stop means while said distal opening is contained within said dilating member and said channel means is a fluid-conducting channel in said pliable shaft connecting said proximal and distal openings.

11. An apparatus for introducing a tube into a dilated nostril, comprising a tube introducer, including:

an elongate, porous sleeve formed from a collapsible material, and having proximal and distal ends with openings at said proximal and distal ends;

an elongate, relatively slender arcuate guiding member attached to said sleeve along a longitudinal sleeve dimension extending between said proximal and distal openings;

a soft, blunt distal tip formed on said guiding member and extending beyond said distal end opening; and a nostril dilator, including:

a dilating means formed from a resilient, porous material and insertable into said sleeve for erecting said sleeve from a collapsed, compact configuration into a tubular configuration and for dilating a nasal passageway into which said tube introducer has ben inserted, said dilating means being compressible when inserted, through said sleeve, into a nasal passageway; and means for conducting fluid from outside a nostril opening to said dilating means when said dilating means is inserted into a nostril.

12. The apparatus of claim 11 further including stop means on said proximal end of said sleeve for preventing the entry of said proximal end into a nasal opening when said device is inserted into a nostril, distal tip first.

13. The apparatus of claim 11 further including means for maintaining said distal opening closed and for yielding in response to a probing force exerted through said sleeve in a direction toward said distal end of said sleeve to open said distal opening.

14. The apparatus of claim 11 wherein said arcuate guiding member comprises a catheter with a distal end opening into said distal tip, a proximal end, and a fluid-conducting passageway connecting said distal and proximal ends of said catheter.

15. The apparatus of claim 14 wherein said distal tip is formed on said distal end of said catheter and comprises a mass of woven, permeable material for wicking fluid outwardly from said distal end.

16. The apparatus of claim 11, wherein said dilating means comprises:

an elongate, arcuate dilating member formed from a resilient, porous material which is compressible when inserted into a nasal passageway, said dilating member having a central axis a blunt, rounded distal end and a proximal end;

a stop means formed on said proximal end of said dilating member for preventing the entry of said proximal end into a nasal opening when said dilating member is inserted into a nostril, distal end first; and an arcuate, relatively slender, pliable shaft disposed substantially in the central axis of said dilating member.

17. The apparatus of claim 16 wherein said means for conducting fluid includes a channel means in said shaft for conducting fluid from a location proximal to said stop means to said dilating member when said dilating member is inserted into a nostril, distal end first.

18. The apparatus of claim 17 wherein said pliable shaft is a catheter with proximal an distal openings and is disposed in said dilating member such that said proximal opening extends out of said stop means while said distal opening is contained within said dilating member and said channel means is a fluid-conducting channel in said pliable shaft connecting said proximal and distal openings.

19. The device of claim 11, wherein the porous sleeve is of a material which is non-self-sustaining and which collapses without internal support, and the arcuate guiding member has a curvature approaching 90 degrees for enabling the apparatus to round the corner at the rear of the nasopharynx.

20. A device for introducing a nasal tube, comprising:
an elongate, porous sleeve formed from a collapsible material, the sleeve having opposite proximal and distal ends with openings at said opposite ends;
an elongate, relatively slender arcuate guiding member attached to said sleeve along a longitudinal sleeve dimension extending between said proximal and distal ends; and
a soft, blunt distal tip formed on said guiding member at the distal end of said sleeve and extending beyond said distal end opening, the distal tip comprising a mass of woven, permeable material for conducting fluid outwardly from said distal end.

* * * * *